United States Patent
Neuland et al.

(10) Patent No.: US 7,114,422 B1
(45) Date of Patent: Oct. 3, 2006

(54) METHOD AND DEVICE FOR PRODUCING A PRODUCT MADE OF STRIP TAPE, ESPECIALLY A MEDICAL PRODUCT AND/OR A PRODUCT CONTAINING ACTIVE SUBSTANCES AS WELL AS FILLABLE RECEPTACLES OR POUCHES WHOSE EDGES CAN BE SEALED

(75) Inventors: Detlev Neuland, West Caldwell, NJ (US); Wolfgang Schafer, Ledgewood, NJ (US); Hans-Rainer Hoffmann, Neuwied (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

(21) Appl. No.: 09/980,199

(22) PCT Filed: May 31, 2000

(86) PCT No.: PCT/EP00/04970

§ 371 (c)(1),
(2), (4) Date: Mar. 8, 2002

(87) PCT Pub. No.: WO00/74618

PCT Pub. Date: Dec. 14, 2000

(30) Foreign Application Priority Data

Jun. 2, 1999 (DE) ................................ 199 25 339

(51) Int. Cl.
B26D 7/06 (2006.01)
B26D 3/00 (2006.01)
B26D 1/22 (2006.01)

(52) U.S. Cl. ..................... 83/29; 83/44; 83/88; 83/100; 83/156; 83/402; 83/407; 83/425; 83/505; 83/659; 83/676

(58) Field of Classification Search ................... 83/98, 83/100, 156, 402, 407, 659, 676, 505, 25, 83/13, 84, 88, 658, 29, 44, 435.2, 425; 28/170, 28/171; 26/7; 242/525.7; 162/194, 286; 270/52.09; 226/97.1–97.4
See application file for complete search history.

(56) References Cited

U.S. PATENT DOCUMENTS 1,790,559 A * 1/1931 Swift, Jr. .................... 226/112
1,980,400 A * 11/1934 Grupe ......................... 270/41

(Continued)

FOREIGN PATENT DOCUMENTS

DE    211 962 C    7/1909

(Continued)

OTHER PUBLICATIONS

Patent Abstract of Japan, vol. 010, No. 375 (M-545), Dec. 13, 1986.

(Continued)

*Primary Examiner*—Kenneth E. Peterson
*Assistant Examiner*—Isaac N. Hamilton
(74) *Attorney, Agent, or Firm*—Birch, Stewart, Kolasch, and Birch, LLP

(57) ABSTRACT

A process for manufacturing a product from strip tape starting from a broad web of material includes the step of separating the web into individual strips with a vacuum roll, conveying each strip in a vacuum conveyor channel, turning the strips on their way to the channel or in the channel by about 90°, leading the strips together at the end of the channel one upon the other and thereafter processing the strips to form the final product.

9 Claims, 3 Drawing Sheets

U.S. PATENT DOCUMENTS

Figure 1:
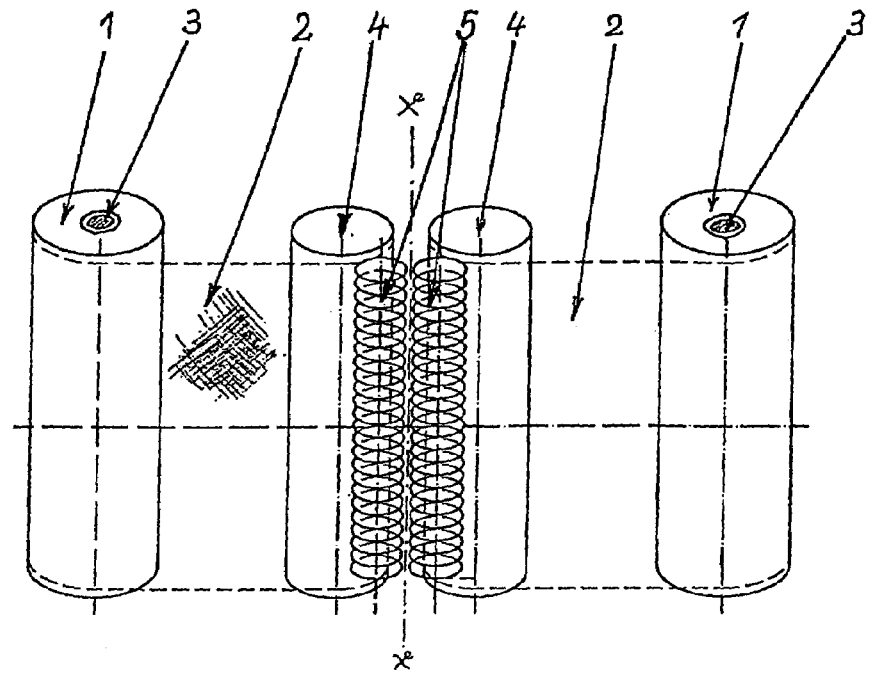

| | | | |
|---|---|---|---|
| 2,293,178 A | | 8/1942 | Stocker |
| 2,332,544 A | | 10/1943 | Winkler et al. |
| 2,862,837 A | * | 12/1958 | Brennan .................... 427/209 |
| 3,192,845 A | * | 7/1965 | Schmidt .................... 396/620 |
| 3,411,728 A | * | 11/1968 | Hall et al. ................ 242/421 |
| 3,556,509 A | * | 1/1971 | Crum ..................... 270/52.08 |
| 3,756,527 A | | 9/1973 | Collins et al. |
| 4,113,247 A | * | 9/1978 | Phillips ..................... 271/264 |
| 4,168,643 A | * | 9/1979 | Takimoto et al. ............ 83/422 |
| 4,349,531 A | * | 9/1982 | Mlodozeniec et al. ...... 424/452 |
| 4,556,441 A | * | 12/1985 | Faasse, Jr. ................. 156/247 |
| 4,666,441 A | * | 5/1987 | Andriola et al. ............ 424/448 |
| 4,693,784 A | * | 9/1987 | Aula et al. ................. 162/202 |
| 4,939,888 A | * | 7/1990 | Katz et al. .................... 53/411 |
| 4,989,487 A | * | 2/1991 | Staley ........................ 83/506 |
| 5,172,621 A | | 12/1992 | Tacchi et al. |
| 5,193,423 A | * | 3/1993 | Bakker ......................... 83/24 |
| 5,224,405 A | * | 7/1993 | Pohjola ......................... 83/24 |
| 5,374,042 A | * | 12/1994 | Ring ....................... 270/52.08 |
| 5,571,361 A | | 11/1996 | Stuerzel |

FOREIGN PATENT DOCUMENTS

| | | |
|---|---|---|
| DE | 27 09 211 A | 9/1978 |
| EP | 0 822 155 A | 2/1998 |
| EP | 0 848 937 A | 6/1998 |

OTHER PUBLICATIONS

Patent Abstract of Japan, vol. 012, No. 208 (M-709), Jun. 15, 1988.

* cited by examiner

METHOD AND DEVICE FOR PRODUCING A PRODUCT MADE OF STRIP TAPE, ESPECIALLY A MEDICAL PRODUCT AND/OR A PRODUCT CONTAINING ACTIVE SUBSTANCES AS WELL AS FILLABLE RECEPTACLES OR POUCHES WHOSE EDGES CAN BE SEALED

This application is the national phase under 35 U.S.C. § 371 of PCT International Application No. PCT/EP00/04970 which has an International filing date of May 31, 2000, which designated the United States of America.

BACKGROUND OF THE INVENTION

The invention relates to a process for manufacturing a product from strip tape, especially a medicinal and/or active substance-containing product such as, for example, dermal or transdermal patches or another administration form, for example for oral application, as well as fillable containers or sealed-margin bags, in which process there is used as starting material a broad, active agent-containing web of material, for instance of sheet-like materials and, in particular, of active substance-containing sheeting or sheet-like active substance, said process comprising at least two of the following steps:
  separating the broad web of material into individual, narrow strips and, if necessary, winding the strips in individual coils or jointly twisting the strips.
  unwinding individual coils or pairs of coils, as required, and assembling at least two strips at a time to form a strip web, or unwinding the strip web wound up from individual strips.
  processing the web of material to form a product made-up of strip tape,
  performing final process steps as, for instance, manufacturing the final product, forming the final application form, laminating the carrier material, segregating, packaging etc.

For manufacturing the above-mentioned products, strip tape consisting of a plurality of individual strips is used. This tape is made by separating a coil of the starting material into individual strips, said coil having a width resulting from the number of strips multiplied by the width of the strips plus edge trimming.

Typically, the resultant strips are wound on reels and are jointly unwound in the number as required and assembled to form webs of material having at least two layers. The manufacture of the stock reels is very labour-intensive, as is the winding and unwinding of the individual strips.

It is possible, here, that the material—which may be an active substance-containing material or a medicinal substance—is stretched impermissibly, with the unavoidable elongation of the material having a negative effect on the dosing accuracy of the medicinal substance.

SUMMARY OF THE INVENTION

It is the object of the present invention to provide a process and a device suitable for carrying out said process which overcome the aforementioned disadvantages, difficulties and technical limitations, and, in particular, enable the manufacture of a strip tape product, especially preferred an active substance-containing product, at reduced expenditure in respect of work and costs and without disadvantageous elongation of the material.

To achieve this object in a process of the kind mentioned at the outset, it is proposed according to the invention
  that a roll of material with a broad web of the starting material be mounted, loosely rotatable, on a take-up mandrel,
  that the web of material be drawn, in its entire width and without subjecting the material to tensile stress, from the roll of material by means of a vacuum roll, or a device comprising two rolls, which unwinds the material gently from the material roll with one of the rolls simultaneously serving as a counter support to the cutting knifes; the material being separated in the process into individual strips in the negative pressure zone of the vacuum roll by rolling a multiple circular knife roll,
  that at the end of the negative pressure zone of the vacuum roll or of the pair of rolls, each strip be drawn from the said vacuum roll or pair of rolls and be introduced in a take-up channel and continuously conveyed therein my means of negative pressure,
  that in the process each strip is turned on its way to the channel or through the channel by about 90°, and
  that at the end of the channels the strips be led one upon the other, at least two at a time, and thereafter conveyed in a, preferably open, groove for further processing under completion to form the final product, to a conversion equipment where the products are finished.

One embodiment of the process provides that for drawing the web of material and separating it into strips in cooperation with the multiple circular knife roll, there is used instead of a vacuum roll, a smooth stripping roll cooperating in a zone where the web of material travels around the roll with a pressure roll and a guide roll.

A device for the manufacture according to the present invention of a product from strip tape, especially of a medicinal and/or active substance-containing product such as, for example, a dermal or transdermal patch or another administration form, for example for oral application, as well as fillable containers or sealed-margin bags, especially for carrying out the process according to the invention,
  is characterized in that:
  as a means for drawing off and separating the web of material a vacuum roll is provided, in whose web-travelling zone the web of material, held by the negative pressure, can be severed into individual strips in cooperation with the multiple circular knife roll,
  to each strip there is associated a vacuum conveyor channel which is designed such that each strip is turned on its way to the channel or through the channel by about 90°, and
  the ends of all the take-up channels 12 are brought together at one site to form a unit and that at that site there are provided guide means and transport means for the further transport to a conversion equipment.

One embodiment of the device according to the invention provides that as means for drawing the web of material and for transport during the separation into strips in cooperation with the multiple circular knife roll, there is provided instead of a vacuum roll, a smooth stripping roll arranged in a zone where the web of material travels around the roll and adapted to cooperate with a pressure roll and a guide roll.

The process according to the invention and the device provided for carrying out the same overcome the aforementioned disadvantages, difficulties and technical limitations of the prior art and, in particular, enable the manufacture of medicinal and/or active substance-containing products at reduced expenditure in terms of work and costs without disadvantageous elongation of the starting material.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DARWINGS

Further details, features and advantages of this invention will become apparent from the following explanation of an embodiment example which is schematically illustrated in the figures.

The figures show:

FIG. 1: a side view of the device

Figure 2:
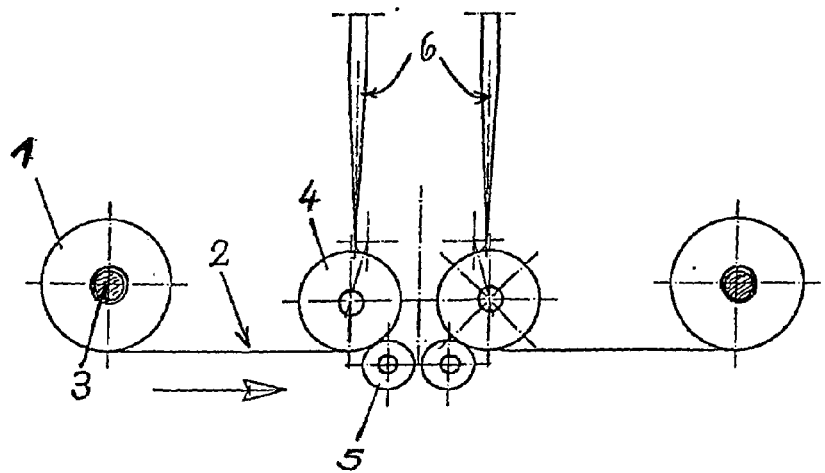

FIG. 2: a plan view of the device according to FIG. 1

Figure 3:
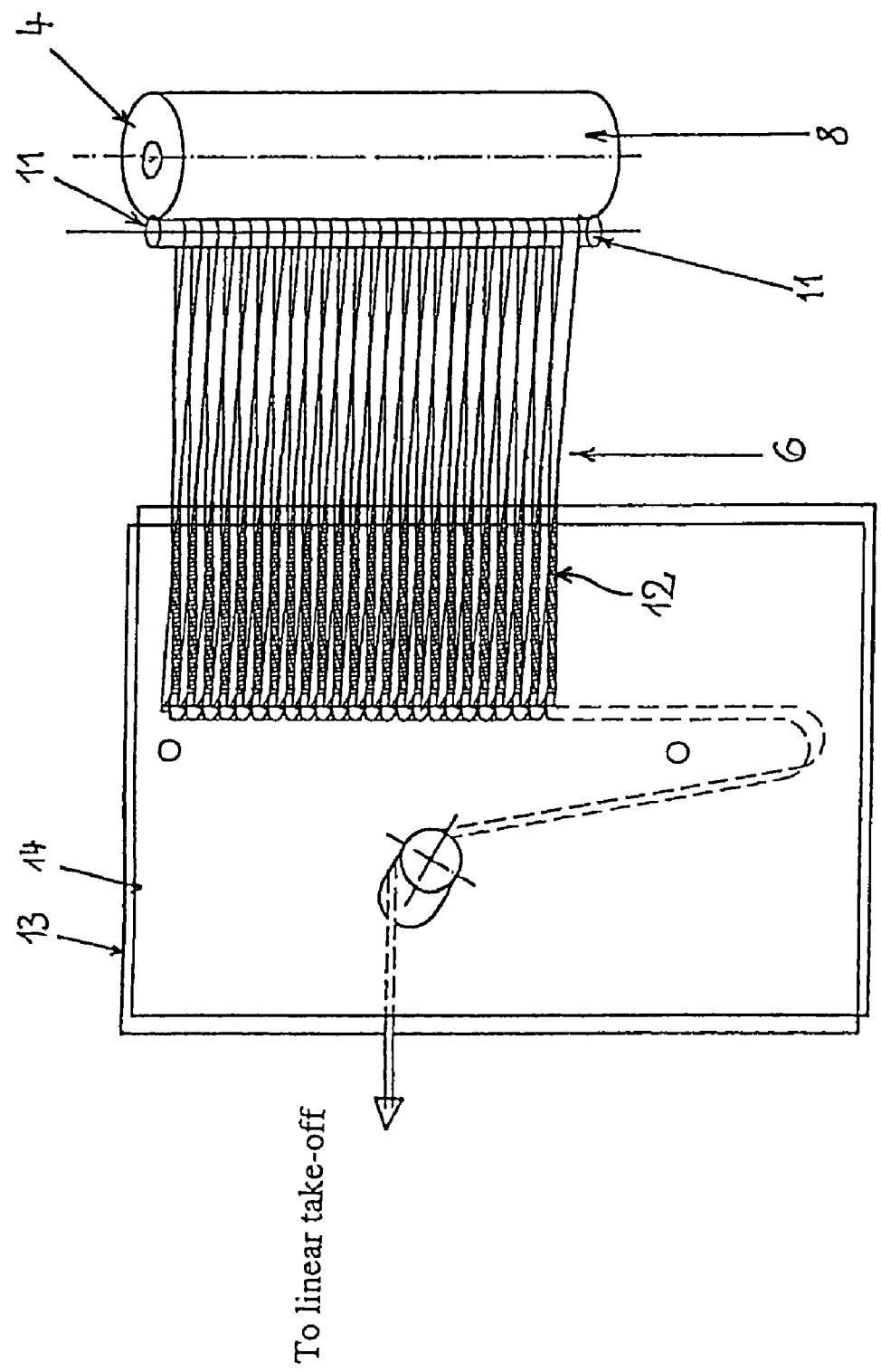

FIG. 3: a partial view of the device with vacuum transport channels disposed at the end of the device.

Figure 4:
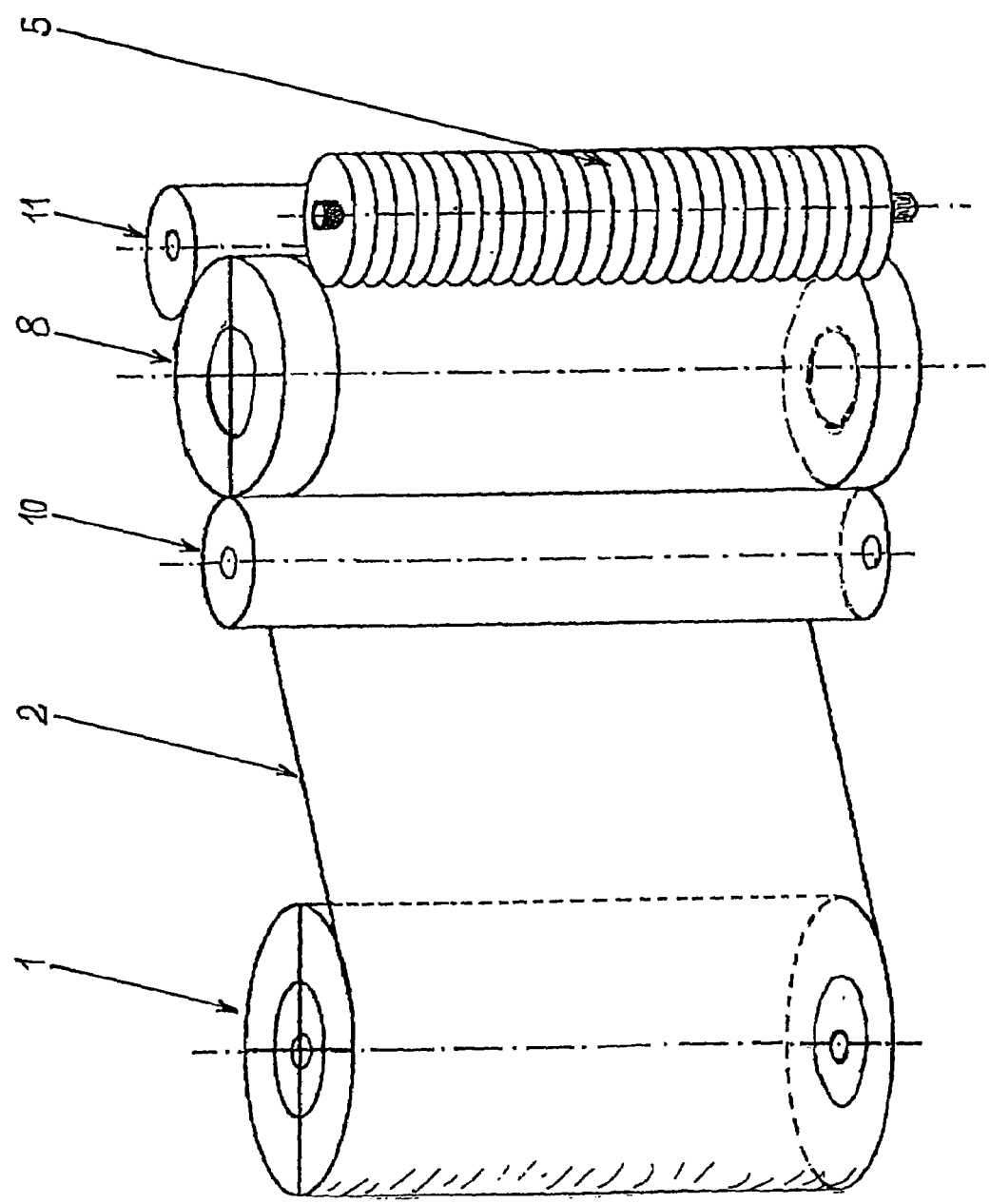

FIG. 4: a view of the device in which a smooth stripping roll is provided instead of a vacuum roll.

DETAILED DESCRIPTION OF THE PREFERRED EMBODIMENTS

The part of the device represented in FIG. 1 shows rolls of material 1 with a web 2 of the starting material in a duplicate arrangement on both sides of a plane of symmetry x—x, said rolls 1 being mounted on take-up mandrels 3, as well as a duplicate arrangement of vacuum rolls 4, and circular knife rolls 5 rolling on said vacuum rolls 4 and the web of material 2 and having a plurality of circular knifes disposed parallel thereto.

The same device is shown in FIG. 2 in plan view, with rolls of material 1, mounting mandrel 3, the material web 2, which can be uncoiled, vacuum rolls 4, circular knife rolls 5, and strips of material 6 cut from the web 2 and running off the said circular knife rolls 5 at the end of the vacuum zone.

FIG. 3 shows, in part in side view and in part in plan view, a vacuum roll 4. However, this may also be a stripping roll 8 aided by a guide roll 11, from which strips 6, cut by a circular knife roll (not shown), are transported in the width of the original web of material 2. For linear take-off of a plurality of strips 6 there are provided vacuum conveyor channels or take-up channels 12, each formed, for example, between two cover plates 13 and 14. Finally, FIG. 4 shows an alternative embodiment of the device wherein as means for drawing the material web 2 and for transport thereof during separation of the web of material in strips 6 in cooperation with a multiple circular knife roll 5 there is provided instead of a vacuum roll a smooth stripping roll 8 which is arranged in a zone in which the material web 2 travels around the roll and is adapted so as to cooperate with a pressure roll 10 and a guide roll 11.

The process and device are uncomplicated, reduce the expenditure of work and costs required heretofore, and enable the manufacture from strip tape of medicinal and/or active substance-containing products of various design, or of fillable containers or sealed-margin bags, while avoiding a disadvantageous elongation of the material, and, in particular, using a starting material in the form of sheet-like material, preferably a sheet-like active substance-containing administration form.

The present invention thus constitutes an optimal solution to the task presented at the outset.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The invention claimed is:

1. A process for providing a plurality of individually stacked strips from a single web of material, the method comprising the steps of:
   providing the single web of material to a multiple circular knife roll;
   cutting the single web of material by the multiple circular knife roll into a plurality of strips having a predetermined width;
   rotating each of the plurality of strips from a first conveyance plane to a second conveyance plane, the second conveyance plane being substantially perpendicular to the first conveyance plane;
   drawing each of the plurality of strips into an individual vacuum conveyor channel;
   feeding each of the plurality of strips through the vacuum conveyor channel such that each of the plurality of strips are conveyed only by a vacuum generated within each vacuum conveyor channel; and
   placing each of the plurality of strips onto one another upon exiting the vacuum conveyor channel so that the plurality of strips are stacked.

2. The method according to claim 1 further comprising the step of:
   cutting the stacked plurality of strips into a predetermined length.

3. The method according to claim 1 wherein the multiple circular knife roll operates in conjunction with a vacuum roll to cut the single web of material into a plurality of strips.

4. A process for manufacturing a medicinal and/or an active substance containing product of at least two strip tapes, said process comprising the steps of:
   drawing a broad web of material in its entire width from a roll of material which is mounted loosely rotable on a take-up mandrel by a vacuum roll;
   conveying said broad web of material by said vacuum roll to a multiple circular knife roll;
   separating said broad web of material into individual strips in a negative pressure zone of said vacuum roll by rolling said multiple circular knife roll;
   drawing each of said individual strips from said vacuum roll and introducing each of said individual strips into a vacuum conveyor channel;
   conveying each of said individual strips through said vacuum conveyor channel;
   turning each of said individual strips on its way to said vacuum conveyor channel or on its way through said vacuum conveyor channel by about 90°;
   allowing said strips at an end of said vacuum conveyor channel to lie one upon the other; and
   thereafter conveying said strips for further processing,
   wherein said individual strips are conveyed through said vacuum conveyor channel and led one upon the other by only a negative pressure.

5. The process according to claim 4 wherein the further processing of said strips comprises the step of manufacturing from said strips a product selected from the group consisting of medicinal and/or active substance containing products, fillable containers and sealed-margin bags.

6. The process according to claim 5 wherein dermal or transdermal patches are manufactured.

7. The process according to claim 5 wherein administration forms for oral application are manufactured.

8. The process according to claim 4 wherein a broad web of sheet-like materials is used.

9. The process according to claim 8 wherein active substance containing sheet-like administration forms are used as said broad web of sheet-like materials.

* * * * *